(12) United States Patent
Onizawa et al.

(10) Patent No.: US 8,760,264 B2
(45) Date of Patent: Jun. 24, 2014

(54) ARTICLE CONVEYING SYSTEM AND SAMPLE PROCESSING SYSTEM

(75) Inventors: Kuniaki Onizawa, Hitachinaka (JP); Yoshio Kiyonari, Hitachinaka (JP); Shigemi Oba, Hitachinaka (JP); Tatsuya Fukugaki, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 25 days.

(21) Appl. No.: 13/386,718

(22) PCT Filed: Jul. 20, 2010

(86) PCT No.: PCT/JP2010/004637
§ 371 (c)(1),
(2), (4) Date: Feb. 7, 2012

(87) PCT Pub. No.: WO2011/013324
PCT Pub. Date: Feb. 3, 2011

(65) Prior Publication Data
US 2012/0133492 A1    May 31, 2012

(30) Foreign Application Priority Data
Jul. 29, 2009    (JP) .................................. 2009-175999

(51) Int. Cl.
*G06K 7/01*    (2006.01)

(52) U.S. Cl.
USPC ..................................................... 340/10.51

(58) Field of Classification Search
USPC ......... 340/10.1, 10.4, 10.5, 10.51, 10.52, 5.1; 705/28; 235/385; 209/511, 517, 518, 209/521, 524, 527, 536, 539, 552, 559, 576, 209/577, 578, 579, 581, 582
See application file for complete search history.

(56) References Cited

U.S. PATENT DOCUMENTS

| 5,087,423 A | | 2/1992 | Ishibashi |
| 5,390,868 A | * | 2/1995 | Kiriake ......................... 242/470 |
| 6,010,075 A | | 1/2000 | Ishifuji et al. |

(Continued)

FOREIGN PATENT DOCUMENTS

| JP | 08-285855 A | 11/1996 |
| JP | 09-158569 A | 6/1997 |

(Continued)

OTHER PUBLICATIONS

English machine translation of Japanese patent (JP 2009-121818 published Apr. 6, 2009) submitted by Applicant in IDS.*

(Continued)

*Primary Examiner* — Jennifer Mehmood
*Assistant Examiner* — Yong Hang Jiang
(74) *Attorney, Agent, or Firm* — Mattingly & Malur, PC

(57) ABSTRACT

An object of the present invention is to provide a sample processing system, wherein writing to each RFID is equalized to eliminate unevenness in the use of sample containers.

The configuration of the present invention can be realized by controlling the numbers of times (write counts) data is written to RFIDs, and by skipping data writing according to frequencies in the use of sample containers.

Setting use information (count) of each IC tag, and comparing the use information with an average value of the use of the IC tags, make it possible to limit the write counts, which enables the equalization of writing to the IC tags, thereby making it possible to uniform the use of the sample containers in the system.

9 Claims, 4 Drawing Sheets

(56) References Cited

U.S. PATENT DOCUMENTS

| | | | |
|---|---|---|---|
| 6,042,002 A | 3/2000 | Ohki et al. | |
| 7,813,974 B1* | 10/2010 | Braum et al. | 705/28 |
| 2004/0094450 A1* | 5/2004 | Whiteman et al. | 206/701 |
| 2005/0036907 A1 | 2/2005 | Shoji | |
| 2007/0143035 A1 | 6/2007 | Petruno | |

FOREIGN PATENT DOCUMENTS

| | | |
|---|---|---|
| JP | 10-010135 A | 1/1998 |
| JP | 11-083865 A | 3/1999 |
| JP | 2004-354333 A | 12/2004 |
| JP | 2005-030855 A | 2/2005 |
| JP | 2009-037670 A | 2/2009 |
| JP | 2009-121818 A | 6/2009 |
| WO | WO9821691 A1 | 5/1998 |

OTHER PUBLICATIONS

European Search Report received in European Application No. 10804077.5 dated Nov. 14, 2013.

* cited by examiner

MEMORY MAP OF IC TAG

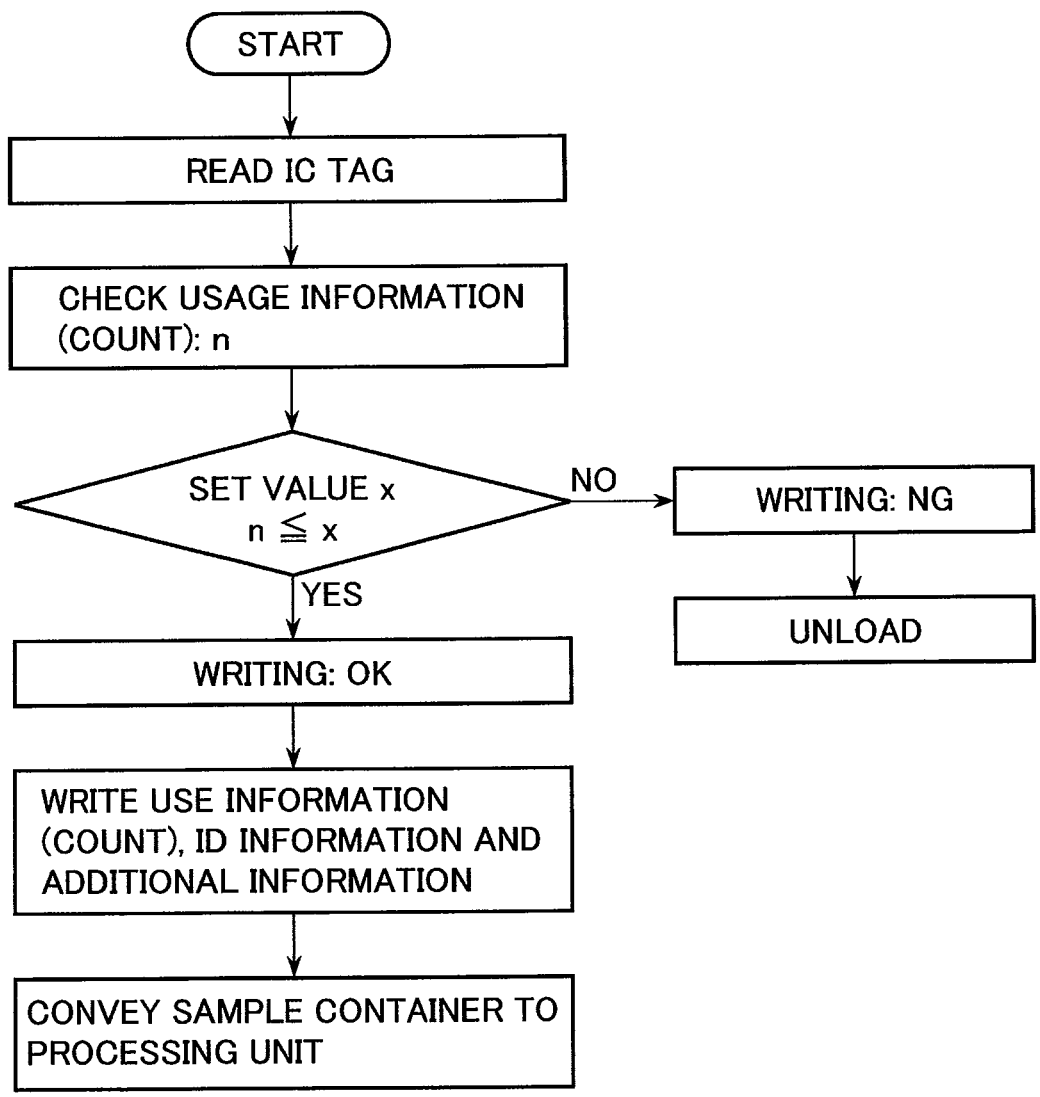

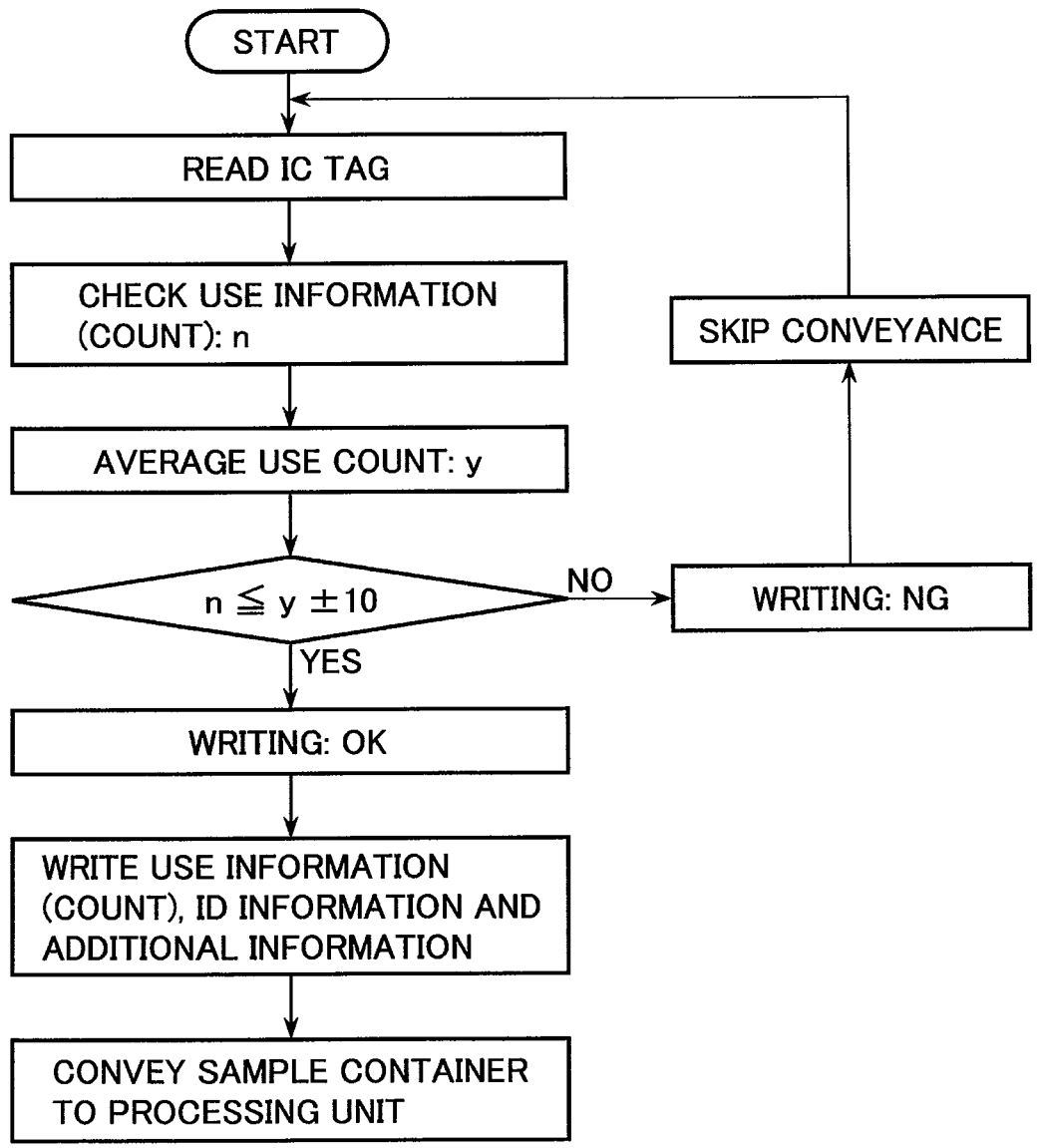

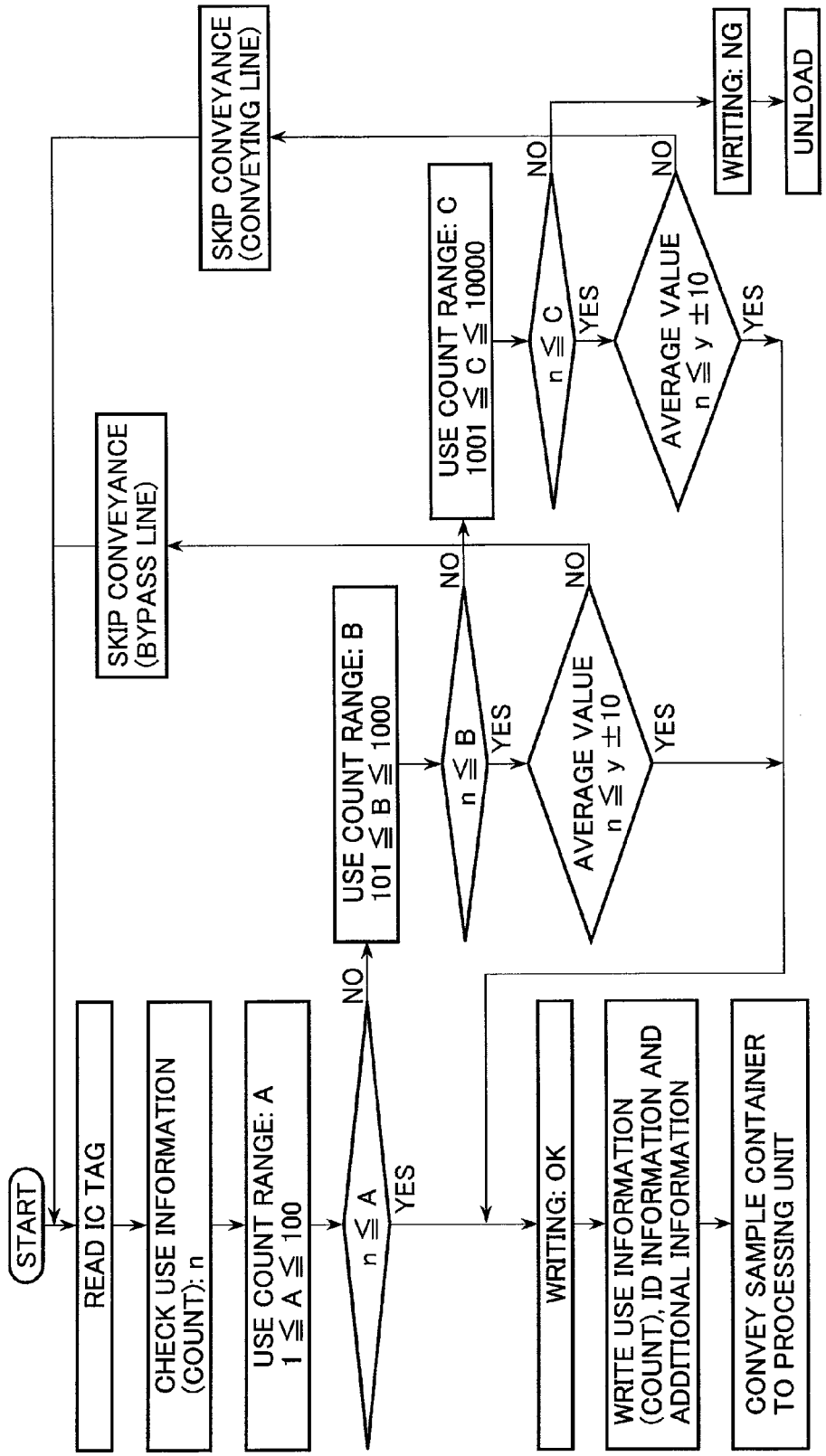

ARTICLE CONVEYING SYSTEM AND SAMPLE PROCESSING SYSTEM

TECHNICAL FIELD

The present invention relates to an article conveying system which conveys an article with the article placed on a conveying table. The invention more particularly relates to an article conveying system in which each of conveying tables is provided with a wireless tag (also called RFID, IC tag or the like), and a sample processing system in which articles to be conveyed are samples.

BACKGROUND ART

When articles are conveyed, it is generally practiced that each article is provided with an information medium, to which identification information is given, so as to identify and manage the each article. Bar code labels, hole IDs each identified by a position of a hole, wireless tags (also called IC tag, RFID or the like) and the like are used as the information media. When bar code labels or hole IDs are used, IDs of articles are fixed and thereby the IDs cannot be reused. Since bar code labels are usually made of paper, they are discarded after each use. In many cases, therefore, bar code labels are directly affixed to articles to be conveyed.

Meanwhile, the information storage capacity of bar code labels is small. When bar code labels need to store a large amount of information, therefore, they are not suitable. In contrast with this, RFIDs have the advantage that the storage capacity thereof is large. However, RFIDs are expensive in comparison with bar code labels, and thus it is not desirable to discard the RFIDs after each use. For this reason, erasing information written to an information recording medium and rewriting information thereto makes it possible to reuse the information recording medium or a conveying table provided with the information recording medium. Patent Documents 1 to 5 disclose examples in which RFIDs are used.

PRIOR ART LITERATURE

Patent Documents

Patent Document 1: JP-2005-30855-A
Patent Document 2: JP-2004-354333-A
Patent Document 3: JP-08-285855-A
Patent Document 4: JP-10-10135-A
Patent Document 5: JP-11-83865-A

SUMMARY OF THE INVENTION

Problems to be Solved by the Invention

Non-volatile semiconductor memories such as flash memories are used in IC tags and the like used as RFIDs. The guaranteed number of times of writing to such non-volatile semiconductor memories is prescribed because the increase in the number of times of writing to each non-volatile semiconductor memory could cause the each non-volatile semiconductor memory to be unwritable and/or unreadable. Meanwhile, when a plurality of articles are provided with IC tags respectively, a specific IC tag may be more frequently used depending on how to use the IC tags, and therefore it could possible that some of the IC tags will have a failure in writing or reading. If such an event occurs, that could influence on the whole conveyance system.

An object of the present invention is to provide an article conveying system and a sample processing system, each of which uses IC tags, wherein the number of malfunctions in devices caused by write and read failures of the IC tags is reduced.

Means for Solving the Problems

In order to achieve the above-described object, according to aspects of the present invention, there are provided configurations as described below.

An article conveying system in which objects to be conveyed are provided with, as identifiers, information recording media equipped with non-volatile semiconductor memories respectively, each of the semiconductor memories having a write count storage mechanism for storing a write count of writing information to the semiconductor memory, the article conveying system comprising:

a write count comparison mechanism for comparing the write count stored in the write count storage mechanism with a predetermined write count limit; and a conveying line control mechanism which controls a conveying line in such a manner that when the write count comparison mechanism determines that, for an object to be conveyed provided with the semiconductor memory as the identifier, the write count of the semiconductor memory is larger than the predetermined write count limit, writing to the semiconductor memory is skipped.

In addition, in the case of the sample processing system, there is provided a sample processing system including, sample container holders, each of which holds a sample container, a conveying line for conveying the sample container holders to a sample processing unit, and an unload unit for supplying the sample container holder to the conveying line, wherein:

the sample container holders are provided with, as identifiers, information recording media equipped with non-volatile semiconductor memories respectively;

each of the semiconductor memories has a write count storage mechanism for storing a write count of writing information to the semiconductor memory; and the sample processing system comprises a write count comparison mechanism for comparing the write count stored in the write count storage mechanism with a predetermined write count limit; and a control mechanism which performs such control that when the write count comparison mechanism determines that, for a sample container holder provided with the semiconductor memory as the identifier, the write count of the semiconductor memory is larger than the predetermined write count limit, writing to the semiconductor memory is skipped.

According to still another aspect of the invention, there is provided a sample processing system including, sample container holders, each of which holds a sample container, a conveying line for conveying the sample container holders to a sample processing unit, an unload unit for supplying the sample container holder to the conveying line, and a collecting unit for collecting a sample container holder in which sample processing is completed by the sample processing unit, wherein:

the sample container holders are provided with, as identifiers, information recording media equipped with non-volatile semiconductor memories respectively;

each of the semiconductor memories has a write count storage mechanism for storing a write count of writing information to the semiconductor memory; and the sample processing system comprises
a write count comparison mechanism for comparing the write count stored in the write count storage mechanism with a predetermined write count limit; and
a conveying line control mechanism which controls the conveying line in such a manner that when the write count comparison mechanism determines that, for a sample container holder provided with the semiconductor memory as the identifier, the write count of the semiconductor memory is larger than the predetermined write count limit, the collecting unit collects the sample container holder in question.

The non-volatile semiconductor memories are usually flash memories, however, any kind of memory can be employed as the non-volatile semiconductor memories so long as the memory is non-volatile and practically has a write count limit.

The article conveying system can be applied to any kind of system so long as the system moves articles through a predetermined route by use of a belt conveyor, a robot arm, a pushing member or the like.

The write count storage mechanism for storing a write count of writing information to the semiconductor memory may be a part of a storage unit of the semiconductor memory, or an external memory other than the semiconductor memory (a volatile memory medium such as a dynamic memory can also be used), or a magnetic recording medium such as a hard disk.

As the write count comparison mechanism for comparing the write count stored in the write count storage mechanism with a predetermined write count limit, in general, a control computer which controls the conveying line may perform the comparison by software. However, it is also possible to perform the comparison by an electric circuit such as a comparator, an operational amplifier and the like.

The conveying line is controlled in such a manner that writing to the semiconductor memory is skipped. In this case, in a general mode, if a mechanism for writing information to the semiconductor memory is disposed at a fixed position, an object to be conveyed is controlled not to pass near the fixed position. However, any kind of control may be performed so long as the writing can be skipped, and if the writing mechanism is movable, the writing may be prohibited by changing a conveyance route according to the move of the writing mechanism.

In general, the sample container holder which holds a sample container corresponds to a holder which is called sample rack or sample holder. The sample rack is usually a rack capable of storing a plurality of sample containers therein; and the sample holder often means a holder which holds one sample container (often having a test tube shape). As a matter of course, the sample rack and the sample holder are not limited to them. The sample rack and the sample holder may have any shape so long as the sample rack and the sample holder are capable of holding a sample container.

Effects of the Invention

The present invention can provide an article conveying system and a sample processing system, each of which uses IC tags, wherein the number of malfunctions of devices caused by write and read failures of the IC tags is reduced.

BRIEF DESCRIPTION OF THE DRAWINGS

FIG. 3 is a diagram illustrating an equalization process flow of writing to an IC tag according to one embodiment of the present invention;

FIG. 4 is a diagram illustrating an equalization process flow of writing to an IC tag according to one embodiment of the present invention; and FIG. 5 is a diagram illustrating an equalization process flow of writing to an IC tag according to one embodiment of the present invention.

BEST MODES FOR CARRYING OUT THE INVENTION

Embodiments of the present invention will be described as below by referring to one embodiment shown in FIG. 1.

Figure 1:
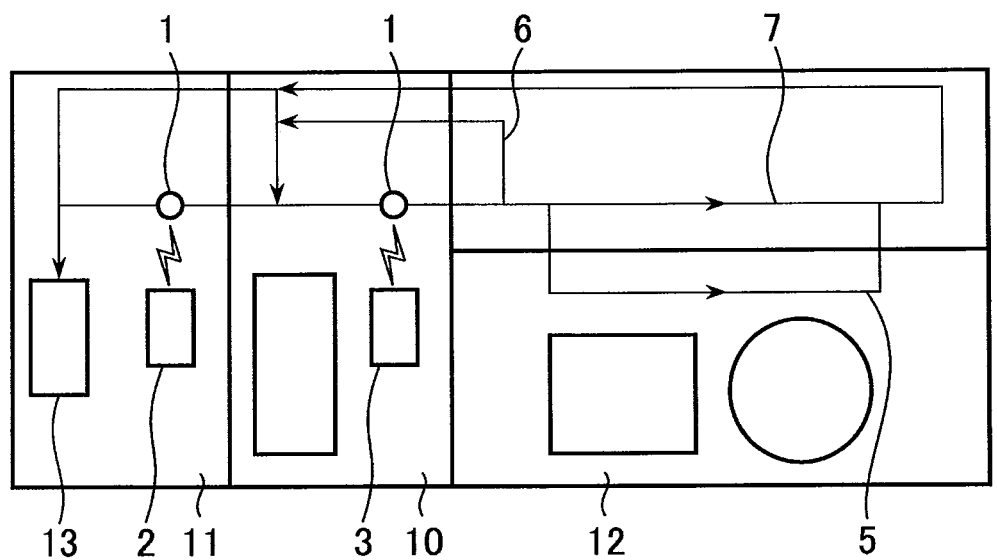
FIG. 1 is a schematic diagram illustrating one embodiment of the present invention.
Figure 2:
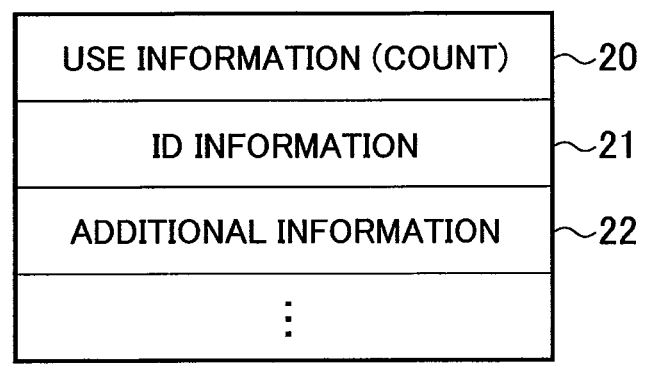
FIG. 2 is a diagram illustrating a memory map of an IC tag according to one embodiment of the present invention.

FIG. 1 is a diagram schematically illustrating an example of a sample processing system which equalizes data writing to an IC tag attached to a sample container 1, wherein data information of the IC tag attached to the sample container 1 is erased by an erasing RFID 2 with which an erase/unload unit 11 is equipped. The sample container 1 is conveyed to a write unit 10 to write data information to the IC tag attached to the sample container 1 by a writing RFID 3. Thereafter the sample container 1 is conveyed to a processing unit 12 through a processing line 5, and is handled in the processing unit 12, and the sample container 1 is then conveyed to the erase/unload unit 11 through a conveying line 7. This sequence of operation is repeated. When the repeated operation causes the number of times the IC tag attached to the sample container 1 is written (write count) to fluctuate, the writing RFID 3 with which the write unit 10 is equipped checks the equalization of the write count on the basis of data of use information (count) 20, and skip conveyance of the sample container 1 to a bypass line 6 or the conveying line 7 is then performed to equalize the write count of writing to the IC tag. FIG. 2 is a diagram illustrating a memory map of the IC tag. Information of the memory map includes the use information (count) 20, ID information 21 and additional information 22. Although the ID information 21, the additional information 22 and the like are erased by the erasing RFID 2 with which the erase/unload unit 11 is equipped, the use information (count) 20 is not erased by the erasing RFID 2. After the equalization is checked by the writing RFID 3 of the write unit 10, the use information (count) 20 is updated at the time of writing. Although not illustrated in the figure, having data information by calculating a checksum value from information such as the use information (count) 20 and the ID information 21 also makes it possible to protect security such as illegal rewriting. In addition, having the data information also achieves an effect of preventing a failure in rewriting and a setting error.

FIG. 3 is a flowchart illustrating an equalization process flow 1 of writing to an IC tag. The writing RFID 3 with which the write unit 10 is equipped reads the IC tag attached to the sample container 1 so as to check the use information (count) 20. The use information (count) 20 is compared with a maximum value x of a use count set in a main controller that is not illustrated. When the use information (count) 20 is smaller than or equal to the maximum value x, writing is allowed, and subsequently the use information (count) 20 of the IC tag is updated, and ID information, additional information and the like are written to the IC tag. The sample container 1 is then conveyed to the processing unit 12 through the processing line 5, and is handled in the processing unit 12. In addition, when the use information (count) 20 is larger than the maximum value x, writing is disallowed, and therefore the sample container 1 is conveyed through the conveying line 7 to an unload unit 13 with which the erase/unload unit 11 is equipped. FIG. 4 is a flowchart illustrating an equalization process flow 2 of writing to an IC tag. The writing RFID 3 with which the write unit 10 is equipped reads the IC tag attached to the sample container 1 so as to check the use information (count) 20. An average use count of the sample container 1 in the sample processing system controlled by the main controller, which is not illustrated, is compared with the use information (count) 20 of the IC tag. When the use information (counter) 20 falls within a range of the average use count, writing is allowed, and subsequently the use information (count) 20 of the IC tag is updated, and ID information, additional information and the like are written to the IC tag. The sample container 1 is then conveyed to the processing unit 12 through the processing line 5, and is handled in the processing unit 12. In addition, when the use information (counter) 20 does not fall within the range of the average use count, writing is disallowed, and therefore skip conveyance is performed through the conveying line 7 to bypass writing to the IC tag. FIG. 5 is a flowchart illustrating an equalization process flow 3 of writing to an IC tag. The writing RFID 3 with which the write unit 10 is equipped reads the IC tag attached to the sample container 1 so as to check the use information (count) 20. The use information (count) 20 is compared with a use count range A set by the main controller that is not illustrated. When the use information (count) 20 is smaller than or equal to the use count range A, writing is allowed, and subsequently the use information (count) 20 of the IC tag is updated, and ID information, additional information and the like are written to the IC tag. The sample container 1 is then conveyed to the processing unit 12 through the processing line 5, and is handled in the processing unit 12. When the use information (count) 20 is larger than the use count range A, the use information (count) 20 is compared with a use count range B. When the use information (count) 20 is smaller than the use count range B, the use information (count) 20 is compared with an average use count. When the use information (counter) 20 falls within a range of the average use count, writing is allowed, and subsequently the use information (count) 20 of the IC tag is updated, and ID information, additional information and the like are written to the IC tag. The sample container 1 is then conveyed to the processing unit 12 through the processing line 5, and is handled in the processing unit 12. In addition, when the use information (counter) 20 does not fall within the range of the average use count, writing is disallowed, and therefore skip conveyance is performed through the bypass line 6 to bypass writing to the IC tag. When the use information (count) 20 is larger than the use count range B, the use information (count) 20 is compared with a use count range C. When the use information (count) 20 is smaller than the use count range C, the use information (count) 20 is compared with an average use count. When the use information (counter) 20 falls within a range of the average use count, writing is allowed, and subsequently the use information (count) 20 of the IC tag is updated, and ID information, additional information and the like are written to the IC tag. The sample container 1 is then conveyed to the processing unit 12 through the processing line 5, and is handled in the processing unit 12. When the use information (counter) 20 does not fall within the range of the average use count, writing is disallowed, and therefore skip conveyance is performed through the conveying line 7 to bypass writing to the IC tag. When the use information (count) 20 is larger than the use count range C, writing is disallowed, and therefore the sample container 1 is conveyed through the conveying line 7 to the unload unit 13 with which the erase/unload unit 11 is equipped. When the skip conveyances are performed through the bypass line 6 and the conveying line 7, each conveying route is changed as a means for smoothly equalizing write counts of writing to IC tags. To be more specific, when a sample is returned to the upstream side of the conveying line 7 through the bypass line 6, a sample rack quickly arrives at the write unit 10. However, when the sample is returned to the upstream side through the conveying line 7, the sample rack takes longer time to return to the upstream side in comparison with the case where the sample is returned through the bypass line 6. For this reason, writing to an IC tag attached to a sample rack to be returned to the upstream side through the bypass line is performed first. This enables the equalization of write counts.

DESCRIPTION OF REFERENCE NUMERALS

1 Sample container
2 Erasing RFID
3 Writing RFID
5 Processing line
6 Bypass line
7 Conveying line
10 Write unit
11 Erase/unload unit
12 Processing unit
13 Unload unit
20 Use information (count)
21 ID information
22 Additional information

The invention claimed is:

1. A sample conveying system comprising:
a conveying line for conveying sample container holders, each of which sample container holders can hold and remove a sample container, to a sample processing unit;
an erase/unload unit for supplying the sample container to the conveying line and for removing the sample container from the conveying line;
a write means for storing a write count of writing information to each of non-volatile semiconductor memories each of which non-volatile semiconductor memories is attached to one of the sample container holders conveyed from the erase/unload unit;
a write count comparison mechanism for comparing the write count of writing information stored by the write means with a threshold value;
a return line for returning the sample container holders, which are finished with processes of the sample processing unit, to an upper stream of the write means;
a conveying line control mechanism for controlling the conveying line and the return line to return each sample container holder including its non-volatile semiconductor memory to skip the writing operation into the semiconductor memories by using the write means and to return the sample container holder into the upper stream of the write means, when the write count comparison mechanism has judged that the write count of the semiconductor memory is larger than the threshold value; and
a reconveying line included in the conveying line, the reconveying line conveying the sample container holder being returned into the upper stream of the write means by the conveying line control mechanism to the write means from the stream of the write means.

2. The sample conveying system according to claim 1, wherein the write count comparison mechanism compares the write count with a plurality of threshold values, and the control for conveying the sample container holder by the conveying line is changed on the basis of the judgment of the write count comparison mechanism which judges whether or not the write count is larger than a plurality of threshold values.

3. The sample conveying system according to claim 2, further comprising a bypass line to return the sample container holder into the upper stream of the write means through a bypass line route which is shorter than the return line, wherein the write count comparison mechanism compares the write count stored in the semiconductor memory with the threshold value, and controls a conveying line in response to whether the return line or the bypass line is used for conveying the sample container holder on the basis of the judgment whether the write count stored in the memory is larger than the plurality of threshold values.

4. The sample conveying system according to claim 1, wherein the write count comparison mechanism compares the write count of writing information by the write means with a plurality of threshold values including a first threshold value and a second threshold value;

wherein the conveying line control mechanism controls the conveying line to convey the sample container holders through a bypass line into the upper stream of the write means when the write count is larger than the first threshold value and smaller than the second threshold value; and wherein the conveying line control mechanism controls the conveying line to convey the sample container holders through the return line to the upper stream of the write means when the write count is larger than the second threshold value, the bypass line being shorter than the return line.

5. The sample conveying system according to claim 4, further comprising:

a write count average value calculation mechanism which determines an average value of write counts of the semiconductor memories included in a plurality of sample container holders; and wherein the write count comparison mechanism includes a control mechanism which permits the writing of information to the semiconductor memory attached to the sample container holder when the write count stored in the semiconductor memory is smaller than a reference value obtained from the average from he write count average valuation calculation mechanism.

6. The sample conveying system according to claim 5, wherein the plurality of threshold values further include a third threshold value, and the sample conveying system further comprises a collecting unit for collecting the sample container holder including the semiconductor memory whose write count is larger than the second threshold value and the third threshold value.

7. The sample conveying system according to claim 1, further comprising a write count changing mechanism for changing the set write count.

8. A sample conveying system comprising:

a conveying line for conveying sample container holders, each of which sample container holders can hold and remove a sample container, to a sample processing unit;

an erase/unload unit for supplying the sample container to the conveying line and for removing the sample containers from the conveying line;

a write means for storing a write count of writing information to each of non-volatile semiconductor memories each of which non-volatile semiconductor memories is attached to one of the sample container holders conveyed from the erase/unload unit;

a write count comparison mechanism for comparing the write count of writing information stored by the write means with a plurality of threshold values including a first threshold value and a second threshold value;

wherein the conveying line control mechanism controls the conveying line to convey the sample container holders through a bypass line into the upper stream of the write means when the write count is larger than the first threshold value and smaller than the second threshold value; and wherein the conveying line control mechanism controls the conveying line to convey the sample container holders through the return line to the upper stream of the write means when the write count is larger than the second threshold value, the bypass line being shorter than the return line;

a write count average value calculation mechanism which determines an average value of write counts of the semiconductor memories included in a plurality of sample container holders; and wherein the write count comparison mechanism includes a control mechanism which permits the writing of information to the semiconductor memory attached to the sample container holder when the write count stored in the semiconductor memory is smaller than a reference value obtained from the average from the write count average valuation calculation mechanism;

a return line for returning the sample container holders, which are finished with processes of the sample processing unit, to an upper stream of the write means; and a conveying line control mechanism for controlling the conveying line and the return line to return each sample container holder including its non-volatile semiconductor memory to skip the writing operation into the semiconductor memories by using the write means and to return the sample container holder into the upper stream of the write means, when the write count comparison mechanism has judged that the write count of the semiconductor memory is larger than the threshold value.

9. The sample conveying system according to claim 8, wherein the plurality of threshold values further include a third threshold value, and the sample conveying system further comprises a collecting unit for collecting the sample container holder including the semiconductor memory whose write count is larger than the second threshold value and the third threshold value.

\* \* \* \* \*